United States Patent [19]
Chen

[11] Patent Number: 5,863,401
[45] Date of Patent: Jan. 26, 1999

[54] SIMULTANEOUS ANALYSIS OF ANALYTES BY IMMUNOASSAY USING CAPILLARY ELECTOPHORESIS WITH LASER INDUCED FLUORESCENCE

[75] Inventor: Fu-Tai A. Chen, Brea, Calif.

[73] Assignee: Beckman Instruments, Inc., Fullerton, Calif.

[21] Appl. No.: 887,566

[22] Filed: Jul. 3, 1997

Related U.S. Application Data

[63] Continuation of Ser. No. 227,801, Apr. 14, 1994, abandoned.
[51] Int. Cl.$^6$ ........................................... C25B 7/00
[52] U.S. Cl. ........................ 204/451; 204/452; 204/455; 436/543; 436/544; 436/546
[58] Field of Search .................................. 204/451, 452, 204/455; 436/543, 544, 546

[56] References Cited

U.S. PATENT DOCUMENTS

| | | | |
|---|---|---|---|
| 4,264,327 | 4/1981 | Blum | 23/230 B |
| 5,137,609 | 8/1992 | Manian et al. | 204/180.1 |
| 5,340,714 | 8/1994 | Katsilometes | 435/6 |
| 5,536,382 | 7/1996 | Sunzeri | 204/451 |

OTHER PUBLICATIONS

Schultz, Nicole M. and Kennedy, Robert T.; "Rapid Immunoassays Using Capillary Electrophoresis with Fluorescence Detection", Analytical Chemistry, vol. 65, No. 21, Nov. 1, 1993.

S.D. Lidofsky, T. Imasaka & R.N. Zare; "Laser Fluorescence Immunoassay of Insulin"; Analytical Chemistry, vol. 51, No. 11, Sep. 1979, pp. 1602–1605.

N. Ichinose, G. Schewedt, F. Schnepel & K. Adachi; "Biomedical and Clinical Chemistry"; Flurometric Analysis in Biomedical Chemistry; Chemical Analysis, pp. 125–126.

Fluorolink–AB™ Cy3™ Labeling Kit Cat. No. A33000, Oct. 1993.

Chen et al., *J. Chromatogr.*, 652(2), 355–60, (CA 120: 70330), 1993.

Schultz et al., "Rapid Immunoassays Using Capillary Electrophoresis with Fluorescence Detection." *Anal Chem.* (65), 3161–3165, 1993.

*Primary Examiner*—Cecilia J. Tsang
*Assistant Examiner*—C. Delacroix-Muirheid
*Attorney, Agent, or Firm*—William H. May; Paul R. Harder; Sheldon & Mak

[57] ABSTRACT

Homogeneous competitive immunoassay methods for simultaneously detecting analytes using capillary electrophoresis and fluorescent detection systems are described. The methods are useful for detecting and/or quantitating the concentration of a plurality of drugs of abuse in a single urine sample using a single assay method.

13 Claims, 5 Drawing Sheets

SIMULTANEOUS ANALYSIS OF ANALYTES BY IMMUNOASSAY USING CAPILLARY ELECTOPHORESIS WITH LASER INDUCED FLUORESCENCE

This is a continuation of application Ser. No. 08/227,801 filed on Apr. 14, 1994, now abandoned.

FIELD OF THE INVENTION

The present invention relates to highly sensitive and rapid homogeneous immunoassays. More specifically, the present invention relates to the simultaneous and homogeneous analysis of haptens employing capillary electrophoresis in concert with detectably labeled haptens and antibodies to the haptens to permit the simultaneous detection and/or quantification of minute concentrations of target haptens. The present invention relates to both the methods of conducting the assays and to the reagents employed therein.

BACKGROUND OF THE INVENTION

The ability to detect and/or quantitate the concentration of a pharmacological agent, metabolite, or toxin is a central aspect of modern diagnosis, management of disease. In some cases, such analytes can be detected directly by assaying their biological activities. In most cases, however, it is more efficient to detect such molecules by virtue of their capacity to specifically bind to antibodies, or by their physical characteristics such as electrophoretic mobility.

Immunoassays are assay systems that exploit the ability of an antibody to specifically recognize and bind to a particular target analyte. The concept of immunoassays is based on a specific chemical reaction between an antibody and its corresponding antigen. Quantitation involves the separation of antibody bound antigen from the free antigen followed by detection of antibody bound antigen or free antigen in solution depending upon the specific analytical scheme. Such assays are used extensively in modern diagnostics (e.g., Fackrell, *J. Clin. Immunoassay* 8:213–219 (1985); Yolken, R. H., *Rev. Infect. Dis.* 4:35 (1982); Collins, W. P., In: *Alternative Immunoassays,* John Wiley & Sons, NY (1985); Ngo, T. T. et al., In: *Enzyme Mediated Immunoassay,* Plenum Press, NY (1985)).

There are many variations of immunoassays and the critical steps are either physical separation or discrimination and detection. Immunoassays that require physical separation are termed heterogeneous immunoassays. In contrast, homogeneous immunoassays are designed such that the removal of bound from unbound species is unnecessary. Because homogeneous assays lack a separation step and are more easily automated, they are more desirable than heterogeneous assays in applications that entail the screening of large numbers of patients.

Analytes present at concentration levels below $10^{-9}M$ are generally assayed using a solid-phase based "sandwich" or competitive method. Typically, in such assays, the antigen of interest competes with a labeled antigen for a judicious amount of antibody. A direct immunoassay is typically a sandwich assay involving two antibodies binding to different antigenic sites of an antigen. One antibody is bound to a solid phase material and is employed to harvest the antigen. The other antibody is labeled and used to generate quantitative information from the bound antigen (Cone, E. J. et al., *J. Forens. Sci.* 35:786–781 (1990); Baugh, L. D. et al., *J. Forens. Sci.* 36:79–85 (1991); Standefer, J. C. et al., *Clin. Chem.* 37:733–738 (1991)).

In order to facilitate the detection of antibody binding, one or more reaction analytes is typically labeled (as with a radioisotope, an enzyme, a fluorescent moiety, a chemiluminescent moiety, or a macroscopic label, such as a bead, etc.) (see, Chard, T. et al., In: *Laboratory Techniques and Biochemistry in Molecular Biology* (Work, T. S., Ed.), North Holland Publishing Company, NY (1978); Kemeny, D. M. et al. (Eds.), *ELISA and Other Solid Phase Immunoassays,* John Wiley & Sons, NY (1988)). Radioisotopes have long been used in immunoassays. O'Leary, T. D. et al., for example, describe a radioimmunoassay for digoxin serum concentrations (O'Leary, T. D. et al., *Clin. Chem.* 25:332–334 (1979)). The difficulty of handling such hazardous materials and the problem of radioactive decay have led to the development of immunoassays that use other labels.

Enzymes, in particular, are now widely used as labels in immunoassay formats. The enzyme-multiplied immunoassay technique (EMIT®, Syva Co.) has been used to assay acetaminophen, cocaine and other analytes (Helper, B. et al., *Amer. J. Clin. Pathol.* 81:602–610 (1984); Campbell, R. S. et al., *J. Clin. Chem. Clin. Biochem.* 24:155–159 (1986); Khanna, P., U.S. Pat. No. 5,103,021; Cone, E. J. et al., *J. Forens. Sci.* 35:786–781 (1990); Baugh, L. D. et al., *J. Forens. Sci.* 36:79–85 (1991); Standefer, J. C. et al., *Clin. Chem.* 37:733–738 (1991); Roberts, D. W. et al., *J. Pharmacol. Exper. Therap.* 241:527–533 (1987); Bartolone, J. B. et al., *Biochem. Pharamcol.* 37:4763–4774 (1988)).

In addition to enzymes, fluorescent moieties are frequently used as labels (see, Ichinose, N. et al., In: *Fluorometric Analysis in Biomedical Chemistry,* Vol 10 110, Chemical Analysis (Winefordner, J. D. et al., Eds.) John Wiley & Sons, NY (1991)). For example, a fluorescence polarization immunoassay format for cocaine has been described (TDx®, Abbott Laboratories, Inc.), and has been found to be approximately equivalent to the EMIT® formats (Schwartz, J. G. et al., *Amer. J. Emerg. Med.* 9:166–170 (1991)). The TDx® format has also been used to assay acetaminophen serum levels (Koizumi, F. et al., *Tohoku J. Exper. Med.* 155:159-(1988); Edinboro, L. E. et al., *Clin. Toxicol.* 29:241-(1991); Okurodudu, A. O. et al., *Clin. Chem.* 38:1040 (1992)), and serum digoxin levels (Okarodudu, A. O. et al., *Clin. Chem.* 38:1040 (1992)). Wong, S. H. Y. et al., have described the use of an automated (OPUS) analyzer to measure digoxin concentration in a monoclonal antibody mediated, fluorescence-based assay protocol (Wong, S. H. Y. et al., *Clin. Chem.* 38:996 (1992)). Lee, D. H. et al. also disclose the use of a fluorescence polarization assay and a chemiluminescent assay format to assay digoxin levels (Lee, D. H. et al., *Clin. Chem.* 36:1121 (1990)).

As indicated, electrophoretic methods have also been used to facilitate the detection of target analytes. Such methods exploit the fact that molecules in solution have an intrinsic electrical charge. Thus, in the presence of an electric field, each molecular species migrates with a characteristic "electrophoretic" mobility which is dependent upon the mass to charge ratio of the molecular species. When this ratio is different from among the various species present, they separate from one another. Under the influence of such a field, all of the variants will move toward a designated charge opposite to the charge of the variants; those having a lower electrophoretic mobility will move slower than, and hence be separated from, those having a (relative) higher electrophoretic mobility.

Immunological electrophoretic methods, such as Immunofixation electrophoresis ("IFE"), Immunoelectrophoresis ("IEP"), and immunosubtraction electrophoresis ("ISE") have been described which combine the capacity of slab gel electrophoretic methods to separate molecular species with the detection capacity of immunoassays. Such assays have been used to detect and quantitate serum proteins.

IEP and IFE are related procedures (Beckman Bulletin EP-2. "Immunoelectrophoresis Applications Guide." (1991)). IFE is a two stage procedure using agarose gel protein electrophoresis in the first stage and immunoprecipitation in the second. In a clinical setting for the analysis of immunoglobulins, a clinical sample (e.g., whole blood, serum, plasma, urine, cerebrospinal fluid) is placed in multiple positions ("lanes") on an agarose gel. When an electric field is applied to the gel-containing sample, the immunoglobulins will traverse the gel from anionic to cationic electrode. Thereafter, antisera comprising antibodies to specific immunoglobulin classes (typically IgG, IgA, IgM, kappa and lambda) are applied to specific lanes. The gel and antisera are incubated, during which time immune complexes form between the specific immunoglobulins and the antibodies. The location of such immune complexes are visualized by staining. By using a reference pattern on the gel, one can then determine the type of immunoglobulin present on the gel. The presence of a particular band is thus indicative of the presence of an M-protein corresponding to a particular immunoglobulin type. Methods of conducting IFE are disclosed by Chen, F-.T. A, U.S. Pat. No. 5,202,006; Chen, F-T. A., U.S. Pat. No. 5,120,413; Hsieh, Y-Z et al., U.S. Pat. No. 5,145,567; all herein incorporated by reference).

The PARAGON® electrophoresis system (Beckman Instruments, Inc., Fullerton, Calif., U.S.A.) is a commercially available system for conducting both IFE and IEP (See also, Gebott et al., U.S. Pat. No. 4,669,363; Pentoney, S. L., U.S. Pat. No. 5,208,466, herein incorporated by reference; Beckman Bulletin EP-3 "Paragon® Serum Protein Electrophoresis II (SPE-II) Applications Guide" (1990); Beckman Bulletin EP-2. "Immunoelectrophoresis Applications Guide" (1991); Beckman Bulletin EP-4 "Immunofixation Electrophoresis Applications Guide" (1991); Beckman Instructions 015-246513-H "Paragon® Electrophoresis System-IFE" (1990); Beckman Bulletin EP-6 "High Resolution Electrophoresis in the Detection of Monoclonal Gammopathies and Other Serum Protein Disorders." (1990); Chen, F-.T. A. et al. *Clin. Chem.* 37:14–19 (1991)).

Immunosubtraction electrophoresis (ISE) is a variation of IFE (Aguzzi, F. et al., *Estratto dal. Boll. 1st Sieroter, Milanese* 56:212–216 (1977); White, W. A. et al., *Biochem. Clin.* 10:571–574 (1986); Merlini, G. et al., *J. Clin. Chem. Biochem.* 21:841–844 (1983); Lui, C-M. et al., U.S. Pat. No. 5,228,960, herein incorporated by reference). In ISE, however, the sample is pretreated with an insolubilized antibody directed to a particular "target" protein. If the target protein is present, it will bind to the antibody and thus be removed from the sample. The sample is then applied to a gel and subjected to electrophoresis. If the target protein had been present in the initial sample, visualization of the proteins in the gel would reveal a "negative band" (i.e. an absence of staining) at the position in the gel where the removed band would have migrated to, had it not been removed by the antibody. Thus, the absence of a particular band is indicative of the presence of the corresponding target protein in the sample.

IEP, IFE and ISE each require multiple steps, and the preparation and use of a separation gel and a signal-generating stain. Thus highly labor intensive nature of these procedures is an obvious impediment in a clinical setting. Additionally, the amount of disposable end-products associated with these procedures can further increase the allied costs associated with these procedures.

In view of the deficiencies of these methods in clinical settings, less labor-intensive methods that permit greater throughput with lower cost have been sought. One such method is "Capillary Electrophoresis" ("CE") (Chen, F-T. A. et al., *Clin. Chem.* 77:14–19 (1991); Nielsen et al., *J. Chromatogr.* 539:177 (1991); U.S. Pat. No. 5,120,413, all herein incorporated by reference). Capillary electrophoresis (CE) is one of the most powerful tools yet developed for the separation of ionic species such as proteins, peptides and other water soluble molecules.

In general, CE involves introducing a sample into a capillary tube, i.e., a tube having an internal diameter of from about 2 $\mu$m to about 2000 $\mu$m (preferably, less than about 50 $\mu$m, most preferably, about 25 $\mu$m or less) and applying an electric field to the tube (Chen, F-T. A., *J. Chromatogr.* 516:69–78 (1991); Chen, F-T. A. et al., *J. Chromatogr.* 15:1143–1161 (1992)). Since each of the sample constituents has its own individual electrophoretic mobility, those having greater mobility travel through the capillary tube faster than those with slower mobility. Hence, the constituents of the sample are resolved into discrete zones in the capillary tube during their migration through the tube. (Heegard, N. H. H. et al., *Anal. Chem.* 64:2479–2482 (1992); Gordon, M. J. et al., *Anal. Chem.* 63:69–72 (1991); F-T. A., U.S. Pat. No. 5,202,006; Chen, F-T. A., U.S. Pat. No. 5,120,413; Hsieh, Y-Z. et al., U.S. Pat. No. 5,145,567). The method is well-suited to automation, since it provides convenient on-line injection, detection and real-time data analysis.

In particular, capillary electrophoresis methods have been shown to permit rapid and efficient separations of proteins. Advantageously, this technique has been extended to include the rapid separation of the constituents of clinical samples which can be accomplished typically in less than 20 minutes. For example, separation of proteins in plasma and serum sample have been attempted by Jorgenson, J. W. et al. (*Science* 222:266–272 (1983)) and Hjerten, S. (*Electrophoresis* 11:665–690 (1990)). The feasibility of routine analysis of serum proteins by CE in an untreated fused-silica capillary has been demonstrated (Chen, F-T. A. et al., *Clin. Chem.* 37:14–19 (1991); Gordon, M. G. et al., *Anal. Chem.* 63:69–72 (1991)). Detection of protein in CE is usually based on the intrinsic ultraviolet (UV) absorbance of the peptide bond at or near 200 nm, which provides a detection limit of about $10^{-5}$M. Fluorescence-based detection assays have, however, also been described (Lee, T. T. et al., *J. Chromatogr.* 595:319–325 (1992)).

One problem associated with current immunochemical analyses is that these procedures are capable of quantifying and analyzing only one analyte at a time. For example, immunochemical analyses such as traditional radioimmunoassay, enzyme immunoassays (EMIT and ELISA) and fluorescence polarization immunoassays (TDX) are limited in their sample throughput and usefulness because they can accommodate only one analyte at a time. There are numerous conditions in which it would be desirable to have the ability to analyze very low concentrations of multiple analytes in a single sample at the same time. For example, screening urine samples for a variety of different drugs, drug metabolites, or the presence of proteins indicative of a variety of diseases is particularly desirable.

The ability to analyze components of urine provides an important source of information to aid in the definition of states of health, disease, and personal health practices. More specifically, urine is a complex mixture containing proteins, lipids, carbohydrates and many smaller-molecule metabolic products. Each component of urine can be considered to provide an image of the serum, reflecting the body's metabolic state. The kidney regulates the body water, excretes metabolic products and toxic substances and maintains the body's electrolytes and pH by means of urine formation. Thus, studies of urine provide important diagnostic information in diseases, not only of the kidney, but also of many other tissues, including the liver, pancreas, blood, bone, muscle, and the urinary tract, gastrointestinal and cardiovascular systems.

Methods for separating and quantitating urine components traditionally involve HPLC techniques which are tedious and typically result in the analysis of only one sample per day. Using CE methods, many more samples can be analyzed per day. However, these analytical approaches involve UV/visible spectrometry based detection and are limited in sensitivity by the intrinsic molecular absorptivities of the species in urine to concentrations of $10^{-5}$ and above.

In view of the importance of accurately detecting and quantitating analytes in samples, it would be desirable to provide processes which combine the advantages of immunoassays, capillary electrophoresis, and fluorescent detection techniques to simultaneously separate and detect very small quantities of analytes. In particular, it would be desirable to provide processes for analyzing urine samples for metabolites using immunoassay procedures and capillary electrophoresis detection techniques. A capillary electrophoresis technique that could additionally be employed to resolve organic analytes (such as pollutants, toxins, etc.) and which could provide a facile means of detection would also be highly desirable. The present invention provides such methods.

SUMMARY OF THE INVENTION

The present invention provides highly sensitive and rapid homogeneous immunoassays which employ capillary electrophoresis in concert with detectably labeled haptens and antibodies to the haptens to permit the simultaneous detection and/or quantification of minute concentrations of multiple target analytes.

In detail, the invention provides methods for simultaneously assaying a sample for the presence and/or the concentration of more than one analyte in the sample, the method including the steps:

(A) incubating the sample in the presence of i) a judicious amount of each analyte labeled with a fluorophore, and ii) antibody capable of specifically binding to each analyte and fluorophore labeled analyte, wherein the incubation is conducted under conditions sufficient to permit the antibody and the analyte and the antibody and the labeled analyte to form an antibody-analyte complex and antibody-labeled analyte complex, respectively;

(B) subjecting an amount of incubated sample of step (A) to capillary electrophoresis, the capillary electrophoresis being conducted under conditions to separate the antibody-labeled analyte complexes from uncomplexed labeled analyte; and (C) detecting each of the labeled-analytes, the detection being accomplished by inducing fluorescence of the fluorophores, and detecting the induced fluorescence; the detected induced fluorescence for each labeled analyte being directly proportional to the concentration of the analyte in the sample.

In accordance with the present invention, preferred analytes are drugs, including drugs of abuse and their metabolites, and preferred samples are clinical samples, including urine, blood, serum, and saliva. The labeled analytes are fluorophore labeled metabolites of analytes of interest or fluorophore labeled analytes of interest. Preferred fluorophores are fluorescing cyanine dyes which are attached to the metabolite or analyte via a labeling reaction. However, other fluorophores can be used including fluorescein, isothiocyanate, rhodamine, phycoerythrin, phycocyanin, allophycocyanin, o-phthaldehyde label, fluorescamine, tetramethylrhodamine and BODIPY.

The invention particularly concerns the embodiment of the above method wherein the fluorophore has the following formula:

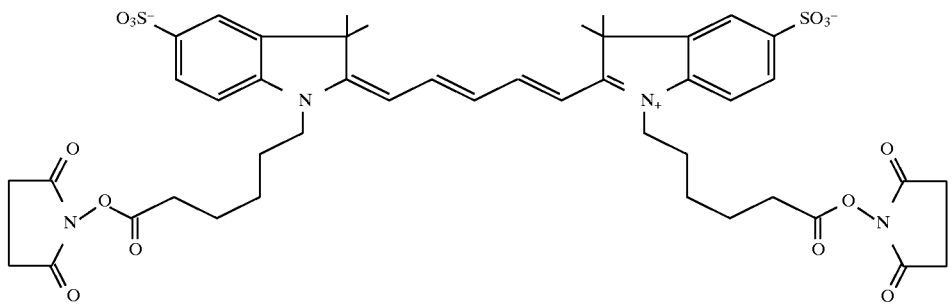

Antibodies suitable for use in the immunoassays described herein include polyclonal antibody, a monoclonal antibody, an Fab fragment, an $F(ab)_2$ fragment and a single-chain immunoglobulin. As long as the antibody or antibody fragment is specific for the analyte of interest, it has utility in immunoassays of the present invention.

DESCRIPTION OF THE PREFERRED EMBODIMENTS

Figure 1:
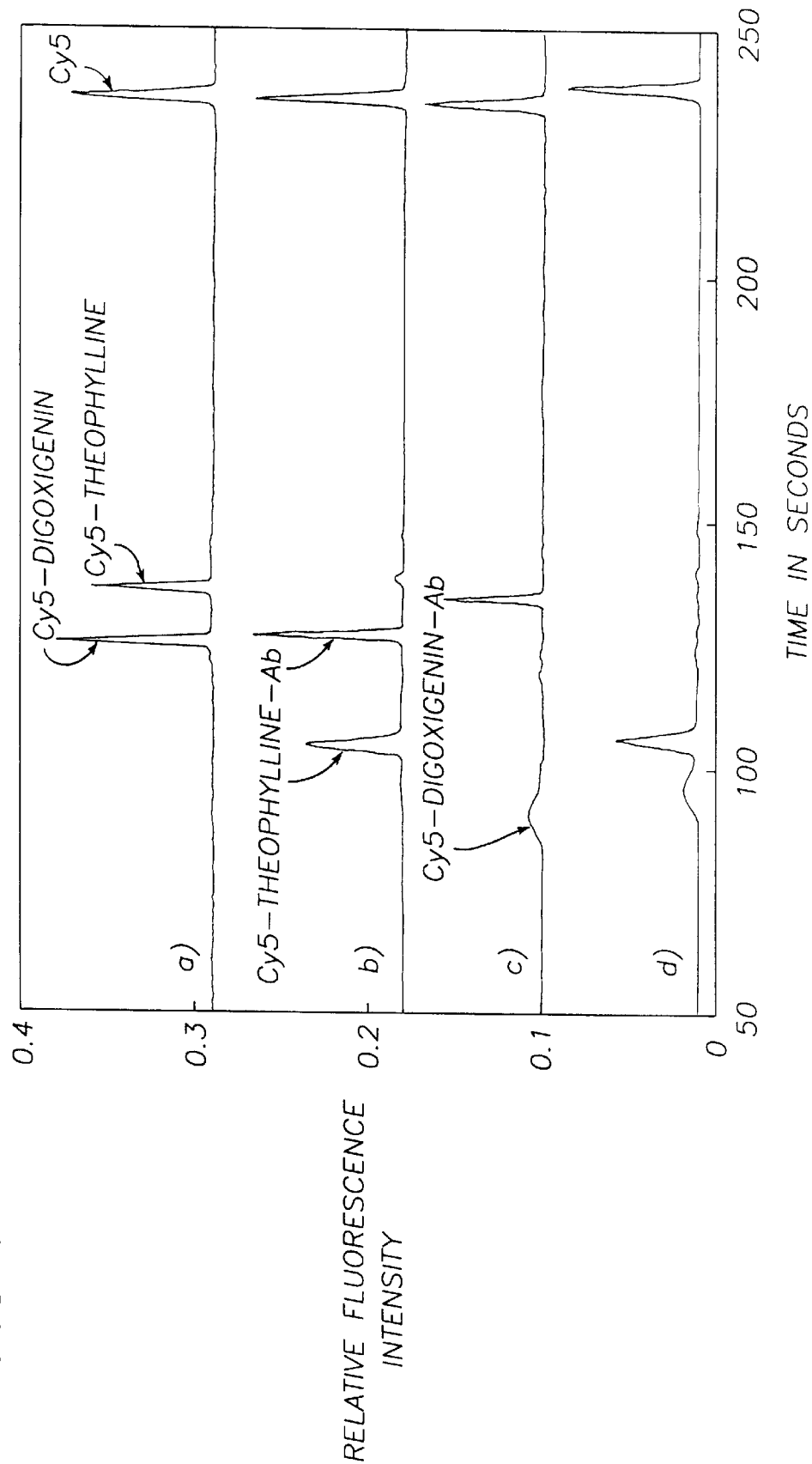
FIG. 1 shows electropherograms associated with antibody titration of digoxigenin and theophylline using CE-LIF techniques. Electropherogram a) is an electropherogram of a solution of Cy-5 labeled digoxigenin at a concentration of 10 nM and Cy-5 labeled theophylline at a concentration of 10 nM. Electropherogram b) is that of the solution of electropherogram a) after titration with theophylline antibody and shows Cy-5 labeled theophylline-antibody complex. Electropherogram c) is that of the solution of electropherogram a) after titration with digoxigenin antibody and shows the Cy-5 labeled digoxigenin-antibody complex. Electropherogram d) shows the results of titrating the solution of a) with antibody for digoxigenin and antibody for theophylline.

I. Overview of the Methods of the Present Invention

The present invention extends the utility of capillary electrophoresis by providing a homogeneous immunoassay format that can be performed in conjunction with capillary electrophoresis in order to permit the detection of very low-level analytes. Indeed, in its most preferred embodiments, the methods of the present invention permit the analysis of analytes even when present at concentrations down to $10^{-9}$M (i.e. sub-$\mu$g/ml). Indeed, at $10^{-10}$M of analytes, the amount of analyte being injected into the CE capillary is merely a few femtograms. Advantageously, the present invention provides a method for analyzing multiple analytes present in complex clinical samples at extremely low concentration. Such an accomplishment had not previously been possible.

In accordance with the present invention, capillary electrophoresis (CE) is used to mediate the separation of the bound from free species present in immunological reactions. Additionally, the methods provide for the free or the bound species to be detected and measured in the presence of numerous potentially interfering substances. This is accomplished by utilizing a uniquely detectable label on selected assay reactants. Moreover, in utilizing a fluorophore as the uniquely detectable label, the assays of the present invention provide high detection sensitivity and thus much lower limits of detectability.

The present invention provides methods for effectively discriminating between an antibody-analyte complex and the free analyte. Furthermore, the present invention provides for the simultaneous analysis for the presence and/or concentration of more than one analyte or analyte metabolic product in a sample, even when the analytes are present in extremely low concentrations.

More particularly, the present invention provides methods for simultaneously assaying a sample for the presence and/or the concentration of more than one analyte in the sample, the method including the steps:

(A) incubating the sample in the presence of i) a judicious amount of each analyte labeled with a fluorophore, and ii) antibody capable of specifically binding to each analyte, wherein the incubation is conducted under conditions sufficient to permit the antibody and the analyte and the antibody and the labeled analyte to form an antibody-analyte complex and antibody-labeled analyte complex, respectively;

(B) subjecting an amount of incubated sample of step (A) to capillary electrophoresis, the capillary electrophoresis being conducted under conditions which cause the antibody-labeled analyte complexes to separate from uncomplexed labeled analyte; and (C) detecting each of the labeled-analytes, the detection being accomplished by inducing fluorescence of the fluorophores, and detecting the induced fluorescence; the detected induced fluorescence for each labeled analyte being directly proportional to the concentration of the analyte in the sample.

Thus, the present invention involves competitive binding reactions in which antibody to each of the analytes competitively binds with sample analytes and labeled analytes which correspond to analytes in the sample. Following the competitive binding reaction the antibody-labeled analyte complexes are separated from the labeled analytes by CE techniques and detected with laser induced fluorescence (LIF). The amount of free labeled analyte is directly proportional to the analyte present in the sample.

In accordance with the present invention, suitable analytes can include any antigen or hapten to which an antibody is available or can be prepared. Thus, virtually any protein or other analyte which acts as a hapten can be analyzed as described herein. In preferred embodiments of the present invention, the analytes are pharmaceutical compounds such as therapeutic or diagnostic drugs, including theophylline and digoxigenin. Importantly, drugs of abuse and their metabolites, such as cocaine, cannabinoids, opiates, PCP marijuana, amphetamines, metamphetamines, heroin and other toxins are particularly amenable to analysis according to the present invention. Similarly, the sample containing the analytes can originate from environmental sources such as waste water, drinking water, air or the sample can be a clinical sample obtained from serum, blood, feces, urine, saliva, or milk. Because the analysis of urine for proteins, drugs, and other health related compounds provides important diagnostic information, preferred samples are clinical urine samples.

The following describes the general scheme for the competitive immuno reaction between a single analyte, a single labeled analyte and an antibody capable of specifically binding to the analyte. In each case below, the analyte is referred to as Ag (or Ag* for labeled analyte), thus indicating that the analyte is an antigen to the antibody.

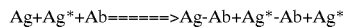

Most therapeutic drugs and the frequently abused drugs and their metabolites are present in urine at concentrations ranging from $10^{-6}$ to $10^{-9}$M. In accordance with the present invention selected analytes and/or their metabolic products can be labeled with a cyanine dye and utilized as a competing species in an immunoassay for the analytes even at these low concentrations. If necessary, the fluoro labeled analyte can be modified chemically to yield a specific mass-to-charge ratio for the compound, thus tailoring the electrophoretic migration of the labeled analyte. In accordance with the present invention, labeled analytes, a urine sample suspected of containing analytes, and antibodies to the analytes can be used in combination with an internal standard to provide for the simultaneous screening of several drugs in a single sample. When a calibration curve is generated for each analyte, the analytes can be quantitated after a single reaction.

A reaction mixture containing drug analytes, labeled drug analytes, and antibodies to the drug analytes reacts according to the following:

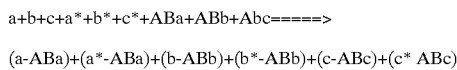

(a-ABa)+(a*-ABa)+(b-ABb)+(b*-ABb)+(c-ABc)+(c* ABc)

wherein:

a, b, and c are free drugs or analytes in a sample;
a*, b*, and c* are fluoro labeled drugs corresponding to a, b, c;
ABa, ABb, and ABc are antibodies to a, b and c, respectively.

In preferred competitive immunoassays of the present invention which involve drug analytes a, b, and c, the competing species a*, b*, and c*, are synthetic reagents and chemically well-defined. That is, each labeled species has a specific charge-to-mass ratio and can be predictably separated by CE. Fluoro labels allow for detection by LIF.

The methods of the present invention are particularly suitable for analyzing proteins, drugs and other pharmacological agents. Such analytes may be detected even if present at concentrations as low as $10^{-11}$M in the sample. Such sensitivity is desirable since it is preferred that the samples being analyzed, especially clinical sample be diluted in an appropriate diluent prior to analysis; such dilution facilitates inter alia achieving a desired analytical ratio, and further augments the sensitivity of the analysis. That is, a non-diluted clinical sample, particularly serum, may contain too much assay interfering protein to permit accurate analysis. Focusing on serum, a most preferred dilution is one part serum to ten parts of an appropriate diluent. However, dilution of up to one part serum to about 100 parts diluent can also be used. The diluent is preferably a lightly buffered saline solution, pH 7.0, such as the ICS™ diluent.

II. The Preferred CE/LIF Methods of the Present Invention

In accordance with the methods of the present invention, the detection and quantification of an analyte is accomplished using CE. In preferred assays, analytes of interest (a, b, c, respectively) are labeled (a*, b*, c*, respectively) and, in the presence of sample thought to contain the analytes, permitted to complex with antibodies (ABa, ABb, ABc, respectively) specific to the analytes (a, b, c) of interest. The immunoreaction is conducted in the presence a judicious amount of antibody and a judicious amount of labeled analyte in order to assure proper quantitative results. The Ab-a* Ab-b*, and Ab-c* complexes thus formed are separated from free labeled a, b*, c* by CE. The amount of free labeled a*, b*, and c* is directly proportional to the amount of a, b, c in the sample.

Typically, the Ab molecules used will be monoclonal antibodies, preferably with affinity constants of $10^{-9}$ or more. In lieu of such antibody molecules, polyclonal antibodies, Fab or F(ab)$_2$ fragments, single chain antibodies, or solubilized receptors or receptor ligands can be employed. In the preferred embodiment of using a monoclonal antibody with an affinity constant of $10^{-9}$M, an antibody concentration of 1.5 mg/ml ($10^{-5}$M) could be employed in the immunoreaction. Such a concentration is capable of binding 10,000 times the level of antigen typically found in serum. Antibodies, including monoclonal antibodies and polyclonal antibodies and antibody fragments which are capable of binding to a large number of antigens and haptens, are commercially available. Alternatively, methods for producing antibodies and antibody fragments utilizing a variety of techniques are known. Those skilled in the art are credited with the knowledge to prepare antibodies to antigens and haptens which are of interest as analytes for purposes of practicing the present invention.

Suitable labels used in conjunction with the above embodiments are fluorescing compounds, including but not limited to fluorescein, isothiocyanate, rhodamine, phycoerythrin, phycocyanin, allophycocyanin, o-phthaldehyde labels, fluorescamine, tetramethylrhodarmine, and "BODIPY". As shown below, particularly suitable labels are cyanine dyes which are commercially available or can be synthesized. Preferred embodiments of the present invention utilize fluorescing cyanine dyes available from Biological Detection Systems, Inc. of Pittsburgh, Pa. These dyes are attractive for use in laser-induced fluorescent applications because their excitation and emission wavelengths are compatible with commercially available and less costly lasers. These fluorescing cyanine dyes are part of a family of dyes known as Cy5. A preferred Cy5 dye has the following structure:

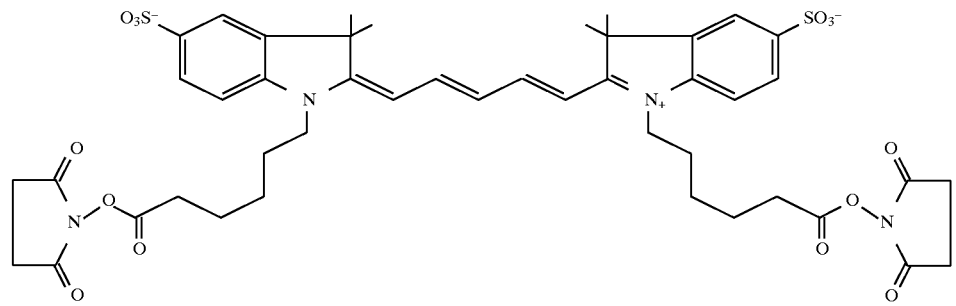

60

Another Cy5 dye has the following structure.

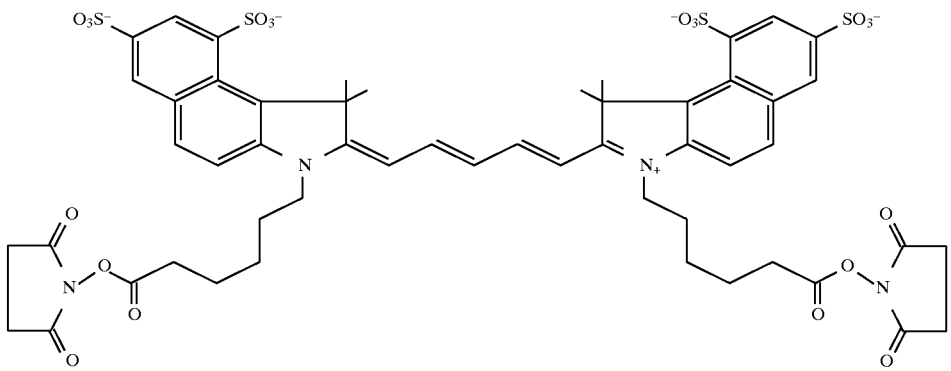

Any suitable method may be used to label the analytes or antigens utilized in the present invention. Performing labeling reactions in which a chromophore or fluorophore is attached to a compound is credited to be within the knowledge of those skilled in the art. When a fluorescing compound contains an active moiety which is capable of reacting directly with a moiety on the analyte, the labeling reaction involves providing conditions for a reaction between the two moieties. In cases where the selected fluorescing compound does not contain a moiety which reacts directly with the analyte of interest, indirect methods in which one or both of the reactants are derivatized in order to provide a reactive moiety may be necessary. The examples provided in this disclosure provide one method of labeling analytes. It is recognized that a wide variety of reactions are suitable. In many cases fluorescing compounds are supplied commercially with active functionalities available for labeling.

For example, 5-carboxytetramethyl-rhodamine succinyl ester (Molecular Probes, Eugene, Oreg.) is available for attaching tetramethylrhodamine (TMR) to an analyte or a desired antigen. For β-phycoerythrin based fluorometric immunoassay by LIF-CE, the sensitivity for analytes are $10^{-11}$M, while that of the synthetic fluorophore such as tetramethylrhodamine, is approximately one order of magnitude lower. Multiple labeling of synthetic fluorophore can be used to provide an arithmetic amplification of LIF signal if they are spaced properly.

Once the immunoreaction has occurred, the reactants and products are subjected to CE under conditions sufficient to resolve the labeled complexes from the labeled analytes. The CE separation technique for these analytes provides a means to separate the bound and free species of the labeled antigen or antibody without the use of a solid support. The application of these separation techniques in conjunction with laser-induced fluorescence detection make possible the homogeneous immunochemical measurement of species at concentrations in the range of $10^{-9}$ to $10^{-10}$M.

Normal CE can be generally separated into two categories based upon the contents of the capillary columns. In gel CE, the capillary tube is filled with a suitable gel, e.g., polyacrylamide gel, and separation of the constituents of the sample is thus predicated by both the size and the charge of the constituents. Despite the speed of analysis, fixed gel CE has several disadvantages, notably, the unpredictability and non-durable nature of the gel material. These factors make fixed gel CE unacceptable in any setting where numerous analytical runs are conducted.

In the second form of CE (i.e. "open" CE), the capillary tube is filled with an electrically conductive buffer solution (Kim, J. W. et al., *Clin. Chem.* 39:689–692 (1993)). A variety of buffers are available for use in CE separations and the choice of buffer and buffer concentration depends upon the analytes being assayed. The preferred processes of the present invention utilize borate buffers having a concentration ranging from 50 mM to 400 mM. Most preferably, the buffer is 200 mM borate, pH 10.00 ±0.25. As the molarity of the buffer increases, the temperature inside the column can increase, and thus, in situations where temperature effects upon the constituents are a factor, lower concentrations of the buffer should be utilized. However, it is to be understood that the disclosed protocol can be accomplished with any separation buffer used in conjunction with the separation of of analytes using coated or untreated columns.

Open CE has many desirable qualities for analysis such as clinical sample analysis, because the analysis does not involve a gel-filled column, the inherent limitations on the number of analytical runs that can be conducted with any particular gel-filled column are avoided; when the capillary column is untreated, the aura of unpredictability which can be associated with coated columns is avoided; the sample size is small (usually on the order of 5 to 200 μl of diluted sample); sample analysis time is fast, i.e., less than about 20 minutes; and the protocol lends itself to automation, thus decreasing the labor skills necessary for efficient and effective sample analysis. The capillary column may be coated on the outside (using, e.g., a polyamide material) for ease of handling.

While the methods of the present invention can use either untreated or coated columns, it is preferred that the columns be untreated. Suitable columns are further disclosed by Guttman, A., U.S. Pat. No. 5,213,669; Burolla, V. P., U.S. Pat. No. 5,198,091; Shieb, C-H., U.S. Pat. No. 5,098,539; all herein incorporated by reference.

Digoxin, a hapten of molecular weight 981, could be labeled with a fluorophore having a molecular weight of approximately 500 and which would ideally be a small molecule containing two sulfonyl or carboxyl groups after labeling. The charge to mass ratio of such an Ag* will be $2/1500$ or $1/750$ and as such will effectively be separated from Ab-Ag* by CE under appropriate buffer conditions. A net positively charged Ag* may be a practical alternative.

In practicing the present invention, determining the presence of labeled compounds subsequent to CE separation is preferably performed by automated or semi-automated means. In the preferred embodiment, wherein a fluorophore is used, the detection is mediated using a laser-induced fluorescence ("LIF") detector. An exemplary detector includes a 1–3 milliwatt helium neon laser (543.5 nm) suitable for exciting the fluorophore. A suitable 2.5 milliwatt green helium-neon laser emitting at 543.5 nm is available from Particle Measuring Systems, Boulder, Colo. The laser output is preferably filtered using a laser line filter and is focused into the detection region of the separation capillary.

Any number of commercially available capillary electrophoresis systems can be utilized to perform the methods described herein. A particularly preferred capillary electrophoretic system is the P/ACE® high performance capillary electrophoresis system (Beckman Instruments, Inc.) (Chen, F-T. A., *Clin. Chem.* 38:1651–1953 (1992); Chen, F-T. A.,*J. Chromatogr.* 559:445–453 (1991); Fu, P. C. et al., *Clin. Chem.* 37:970 (1991); Chen, F-T. A., *Clin. Chem.* 37:1061 (199); Gordon, M. J. et al.,*Anal. Chem.* 63:69–72 (1991), all also herein incorporated by reference). Such instruments are most preferred in that normalization of the electropherograms can be accomplished via on-board computer software (such as System Gold® software (Beckman Instruments, Inc., Fullerton, Calif., USA). In preferred embodiments, the detection system will be integrated into the P/ACE® system using a laser headcoupler to a standard SMA-905 fiber connector to the P/ACE system with LIF detector (available from OZ Optics, Ontario, Canada). The fluorescent emission is preferably collected and collimated using a parabolic reflector which holds the capillary at its focus, and a scatter mask is preferably placed across the front of the parabola in the plane of intense laser scatter. The collimated emission is passed first through a notch filter (543.5 nm blocking), then through a 9 nm band pass filter centered at 580 nm (such filters are available from Barr Associates, Westford, Mass. and from Oriel, Stratford, Conn.). Detection is preferably accomplished using an end-on type photomultiplier tube (such as R374, Hamamatsu).

The CE immunoassay method of the present invention, when combined with LIF signal detection, is capable of simultaneously assaying multiple analytes at concentrations of $10^{-9}$ to $10^{-10}$M. Indeed, methods described herein allow for detection limits in the $10^{-12}$ to $10^{-11}$M range for most fluorophores (cyanine dyes, fluorescein, tetramethylrhodamine, and "BODIPY" for example). CE/LIF immunoassay formats thus meet the requirements of most clinical assays. The use of such fluorophores in combination with high sensitivity laser induced fluorescence (LIF) detectors thus permit the detection of analytes at concentrations that are 4–6 orders of magnitude lower than can be detected by measuring optical absorbance. Detection limits in this range permit many applications that were not previously possible or practical.

As indicated, evaluation of CE is typically visually oriented, i.e. the electropherograms of samples are evaluated to determine the presence of peaks. The areas beneath a peak corresponds to the concentration of the analyte being assayed. Typically, the electropherograms are a plot of detection units (such as fluorescence units) on the vertical axis, and time of constituent traversal through the column to a detection region on the horizontal axis. Results can also be derived in terms of a unit value, typically derived from the areas bounded by the individual peaks.

In order to compare two electropherograms (or the comparative areas beneath the peaks), it is preferred that the electropherograms be normalized. Typically, normalization involves three steps: (1) baseline normalization; (2) fluorescence normalization; and (3) time normalization.

Baseline normalization is typically accomplished by adjusting the electropherograms such that each has a common horizontal baseline; beneficially, this merely requires shifting upward or downward the entire electropherogram in the case where the initial baseline is below or above the zero axis, respectively. Baseline normalization allows for creation of a common horizontal axis.

Fluorescence normalization is preferably accomplished by adjusting the electropherograms based upon the most prevalent protein component in serum, albumin, or with another protein calibrator. Typically, the electropherogram peak associated with calibrator is the "tallest" peak. By selecting a single absorbance maximum for the calibrator, all of the peaks within the electropherogram will be proportionately adjusted. Absorbance normalization thus rectifies differences in, for example, the respective amounts of sample being analyzed.

Time normalization is principally accomplished in order to place the resulting electropherogram results within a constant region. Preferably, this is accomplished by the use of two "markers" which are added prior to the analysis of the treated and untreated samples. The markers are selected such that they are capable of traversing the capillary column and being detected at respective times that bracket the detection times of the sample constituents. Thus, if the detected sample constituents are detected at different times (due to, e.g., variability in the amount of sample analyzed), the relative detection times of the two sets of constituents can be normalized using the markers. In an alternative embodiment of such time normalization, the markers may be selected such that they will bracket the position of the analyte-antibody complex.

Time normalization, like fluorescence normalization, is accomplished such that the relative areas beneath the individual electropherogram peaks remain the same; such normalization merely allows the two electropherograms to be accurately compared to each other. Methodologies for such time normalization are disclosed by Chen, F-T. A., U.S. Pat. No. 5,139,630, which is incorporated fully herein by reference. Methods for improving signal-to-noise ratios in electropherograms are disclosed by Anderson, P. D., U.S. Pat. No. 5,098,536, herein incorporated by reference.

Once electropherograms are normalized using internal standards and normalization techniques, it is within the skill of those knowledgeable in the art to determine the concentration of the simultaneously detected analytes. This is accomplished by generating standard concentration curves for each analyte and using an internal standard to generate the electropherograms used to gather data for the standard curve. The standard curves are typically normalized curves of analyte concentration vs. peak area or peak height, the internal standard being used to obtain the normalized peak area or peak height. By comparing the peak heights or peak areas obtained from the electropherogram of each immunoassay reaction with the peak height or peak area or the standard curve for each analyte, the analyte concentration can be established.

Having now generally described the invention, the same will be more readily understood through reference to the following examples which are provided by way of illustration, and are not intended to be limiting of the present invention.

EXAMPLE 1

The following describes methods for fluorophore labeling PCP, morphine, digoxigenin and theophylline for use in assays for simultaneously determining these drugs in urine in accordance with the present invention.

Fluorescing cyanine based dyes were purchased from Biological Detection System of Pittsburgh, Pa. One dye, Cy5 has the following structure:

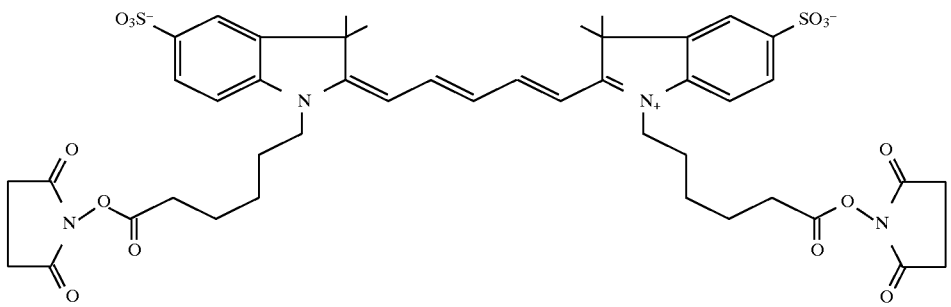

A second cyanine type dye, Cy5.5 has the following structure:

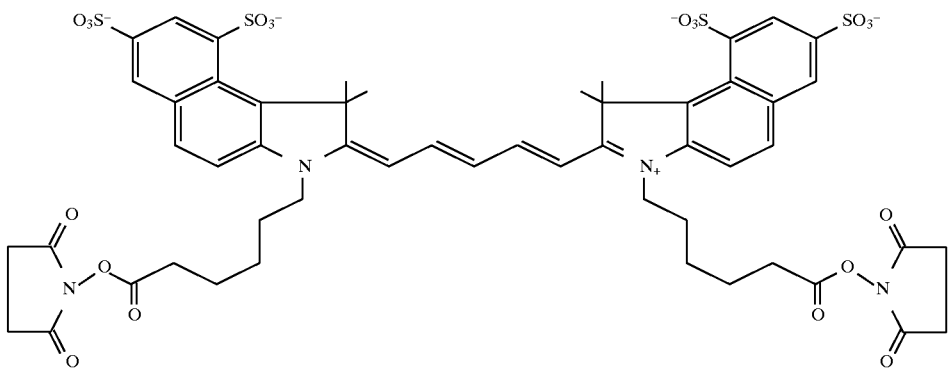

In order to label digoxigenin, 30 nmoles of digoxigenin-3 amine (purchased from Molecular Probes, Eugene, Oreg.) in 50 μL dimethylformamide was reacted with 80 nmoles of Cy5 in 50 μL of 50 mM phosphate buffer adjusted to pH 7.5. The reaction was monitored using capillary electrophoresis and LIF detection to observe a decrease in Cy5 concentration and an increase in Cy5 labeled digoxigenin. The Cy5 labeled digoxigenin was purified by HPLC on a Beckman System Gold with a reverse phase column, Poros R2/H (4.6 mm×100 mm available from PerSeptive Biosystems, of Cambridge, Mass.).

Theophylline was labeled with Cy5 using the same procedure. Theophylline 8-butyric acid was the reactive theophylline reagent for the labeling reaction. Similarly, morphine was labeled with Cy5 using normorphine available from Sigma Biochemical as the reaction reagent for the labeling reaction.

PCP was labeled with Cy5.5 by reacting 20 nmoles of 2-aminoethyl-succinyl-3-amino-PCP in 50 μL of dimethylformamide with 80 nmoles of Cy5.5 in 50 μL of 50 mM sodium bicarbonate, adjusted to pH 8.5 at room temperature for 1 hour. The labeling reaction was monitored using capillary electrophoresis with LIF detection to observe the decrease in amount of Cy5.5 in the reaction mixture and an increase in the amount of Cy5.5 labeled PCP. Cy5.5 labeled PCP was purified on a Beckman System Gold LC using a 168 diode array detector with a reverse phase column (Poros R2/H, 4.6 mm×100 mm from PerSeptive Biosystems, Cambridge Mass.). Buffer for the purification was methanol and 20 mM phosphate at a pH of 6.0.

EXAMPLE 2

In order to show that antibody to digoxigenin and theophylline specifically bind to labeled digoxigenin and theophylline, the labeled drugs were titrated with appropriate antibody as described in this Example. Antibody to digoxigenin was obtained from Boehringer Mannheim Biochemical of Carmel, Ind. Monoclonal antibody to theophylline was obtained from Beckman Instruments, Inc., Brea, Calif. FIG. 1 illustrates the titration reactions. The electropherograms of FIG. 1 were obtained on a P/ACE 2100 electrophoresis system available from Beckman Instruments of Fullerton, Calif. The capillary column, purchased from Polymicro Technologies of Phoenix, Ariz., was 27 cm in length with 20.5 cm to detector window and 20 μm internal diameter. The detection system was a 20 milliwatt red helium-neon laser emitting at 543.5 nm purchased from Melles Griot, Irvine, Calif. A laser headcoupler to a standard SMA-905 fiber connector to the P/ACE system with detector was a product of OZ optics, of Ontario, Canada. The fluorescence signal was collected through a narrow band filter of 690 nm while the laser beam was rejected by a notch filter at 632.8 nm purchased from Barr Associates of Westford, Mass. The buffer utilized in the CE procedure was 200 mM borate buffer at pH 10.2, prepared by filtering the appropriate concentration of buffer through a 0.45 μm filter prior to use. Drug standards used in the experiments were purchased from Sigma Biochemicals of St. Louis and Serva Biochemicals of Westbury, N.Y.

Electropherogram a) was obtained prior to the titration and illustrates Cy5-labeled digoxigenin at 10 nM concentration and Cy5-labeled theophylline at 10 nM concentration. Cy5 at 4 nM concentration is shown at about 240 seconds and is used as the internal standard.

Electropherogram b) of FIG. 1 shows the results of titrating the mixture of electropherogram a) with antibody to theophylline. The Cy5 labeled theophylline-antibody complex appears at about 110 seconds and the Cy5 labeled theophylline almost disappears. The Cy5 labeled digoxigenin remains and the Cy5 internal standard is also present. Electropherogram c) shows the results of titrating the mixture of electropherogram a) with antibody to digoxigenin. Cy5 labeled digoxigenin-antibody complex appears at about 85 seconds, the Cy5 labeled digoxigenin disappears and the Cy5 labeled theophylline remains along with the Cy5 internal standard. Finally, electropherogram d) shows the results of titrating the mixture of electropherogram a) with antibody to theophylline and antibody to digoxigenin. This experiment clearly shows the specificity of these labeled analytes to the appropriate antibody and shows that the two drugs can be simultaneously reacted and assayed.

EXAMPLE 3

In order to demonstrate the competitive binding assay of morphine using CE and LIF detection, the labeled morphine obtained in Example 1 was reacted with antibody to morphine obtained from Biodesign International of Kennebunkport, Me. The antibody was diluted in PBS containing 2 mg/mL BSA and then added to a solution of Cy5 labeled morphine and morphine at varying concentrations. The reaction products were analyzed by capillary electrophoresis using LIF detection in the same manner as described in EXAMPLE 2.

Figure 2:
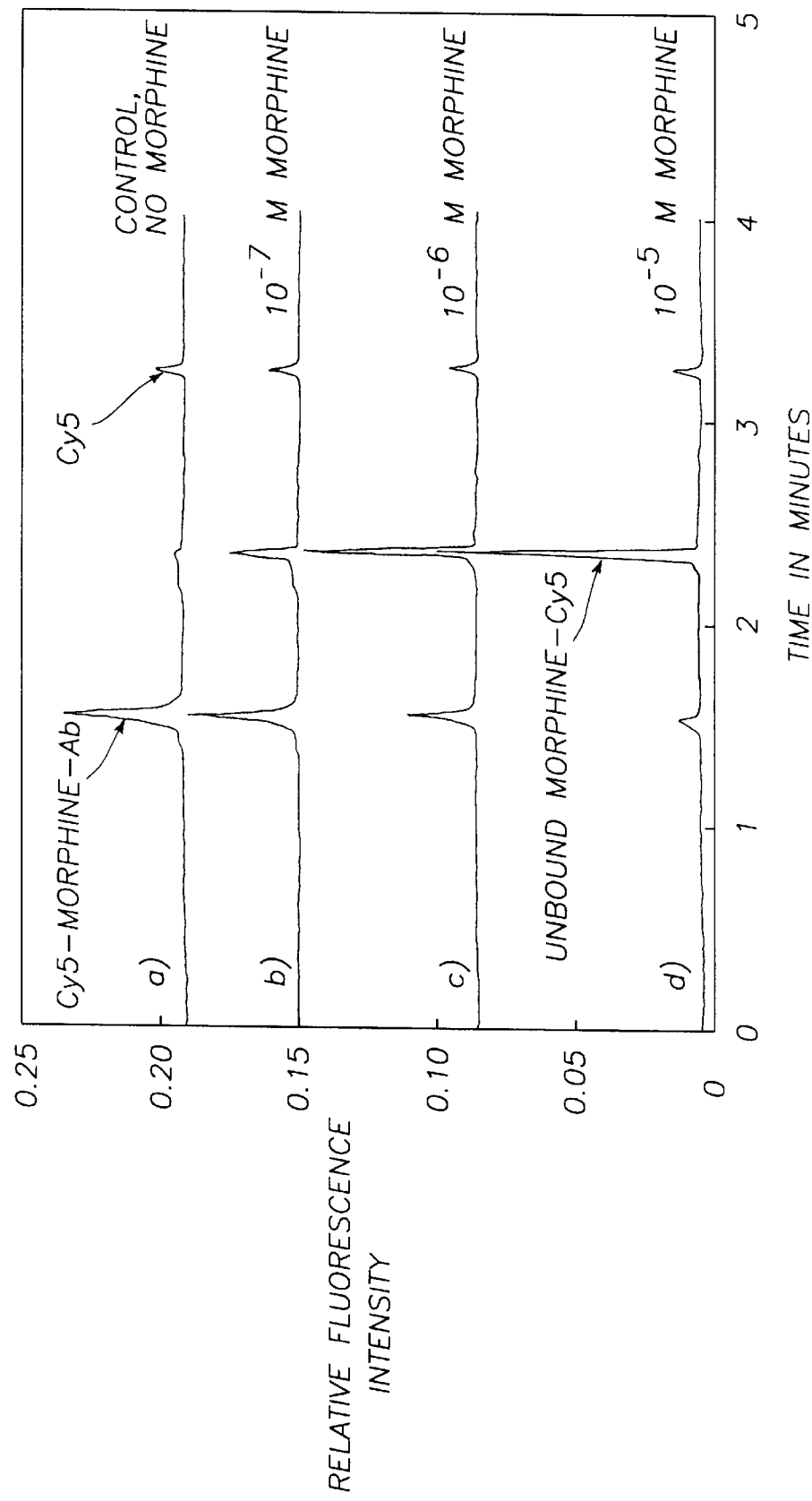
FIG. 2 shows a series of electropherograms showing competitive binding assays of morphine by CE-LIF using different concentrations of Cy-5 labeled morphine and morphine antibody.

FIG. 2 illustrates the results of the competitive binding assays. Electropherogram a) shows the results using no morphine analyte (0 concentration control). Little Cy5 labeled morphine is observed in this electropherogram because no unlabeled morphine is present to compete with the labeled compound (at about 2.3 minutes). Electropherogram b), c) and d) show the result of increasing concentrations of morphine which competes with labeled morphine for the antibody. The greater the amount of morphine present, the less labeled morphine reacts with the antibody. Thus, more labeled and uncomplexed morphine appears on the electropherogram with increasing unlabeled morphine concentration. The amount of unlabeled analyte present is related to both the amount of unbound and labeled morphine and the amount of labeled morphine-antibody complex observed at about 1.5 minutes.

EXAMPLE 4

In order to demonstrate that antibody to morphine displays cross reactivity with different morphines, morphine antibody used in EXAMPLE 3 was reacted in the present of the Cy5 labeled morphine obtained in EXAMPLE 1 and various opiates. The results of the cross reactivity reactions were analyzed using capillary electrophoresis and LIF detection according to the method described in EXAMPLE 2.

Figure 3:
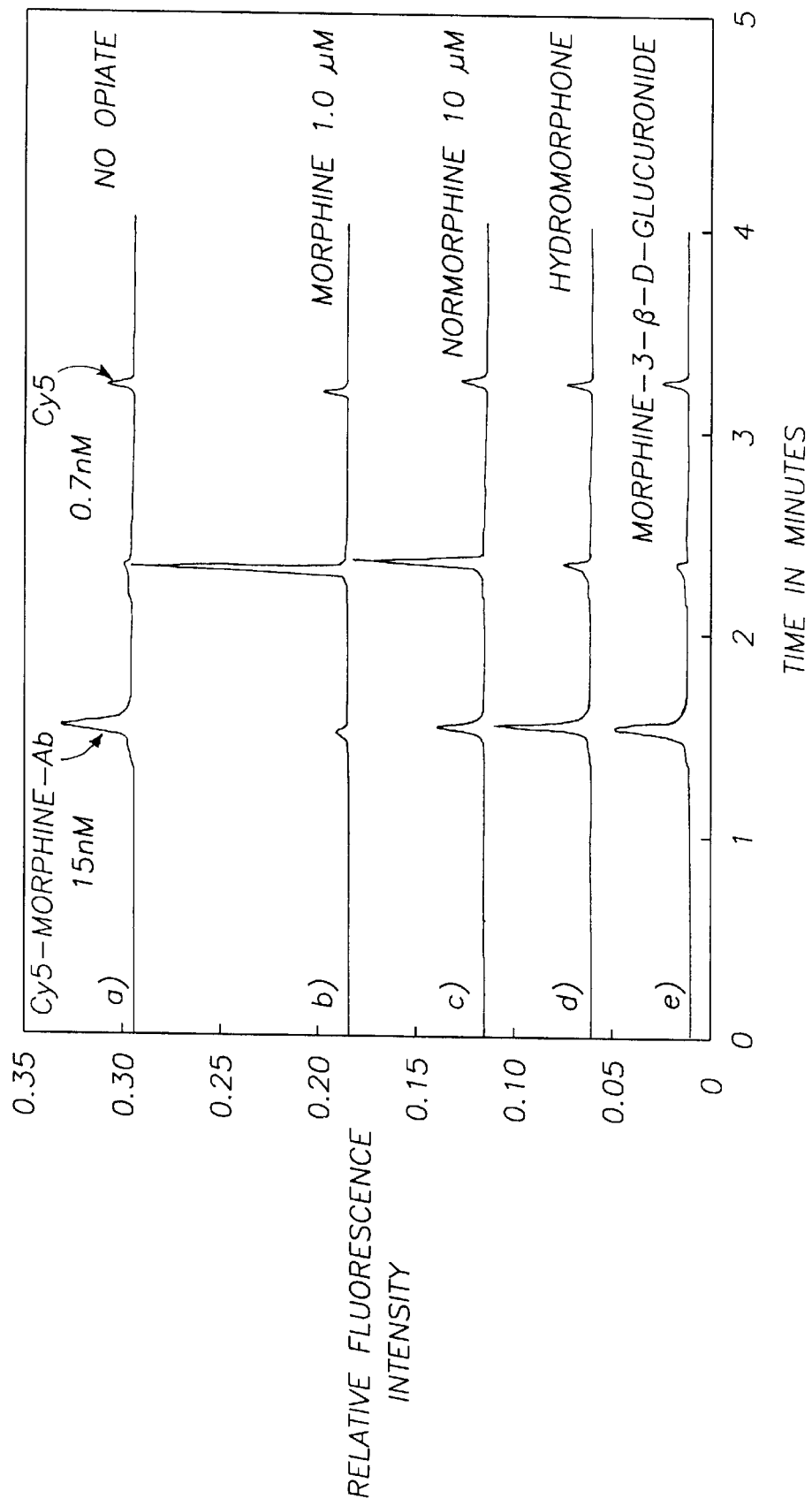
FIG. 3 shows electropherograms which demonstrate the cross reactivity of opiates and morphine with antibody.

FIG. 3 illustrates the results of these experiments. Electropherogram a) shows no opiates added, and labeled morphine reacted with the antibody. Electropherograms b), c), d), and e) illustrate the results of reacting different opiates at different concentration with the antibody. The results show that the competitive binding assay proceeds and cross reactivity is demonstrated.

EXAMPLE 5

Figure 4:
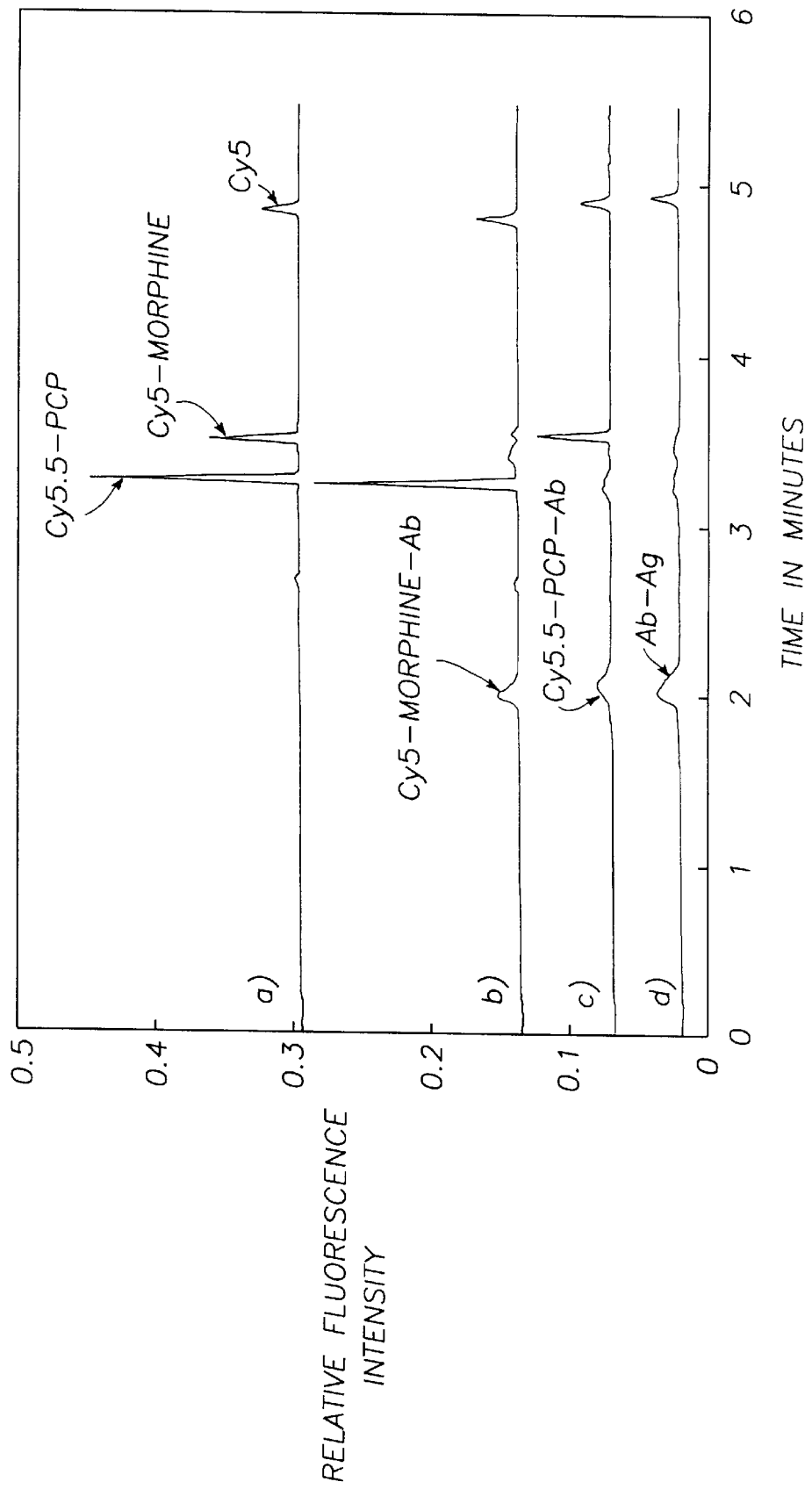
FIG. 4 shows electropherograms associated with an antibody titration of morphine and PCP using CE-LIF techniques. Electropherogram a) is an electropherogram of a solution of Cy-5.5 labeled PCP at a concentration of 10 nM and Cy-5 labeled morphine at a concentration of 10 nM. Electropherogram b) is that of the solution of electropherogram a) after titration with morphine antibody and shows Cy-5 labeled morphine-antibody complex. Electropherogram c) is that of the solution of electropherogram a) after titration with PCP antibody and shows the Cy-5 labeled PCP-antibody complex. Electropherogram d) shows the results of titrating the solution of a) with antibody for PCP and antibody for morphine.

In order to demonstrate the reactivity of labeled Cy5 labeled morphine and Cy5.5 labeled PCP with their appropriate antibodies, the labeled drugs obtained in EXAMPLE 1 were titrated with antibodies to the drugs. The titration products were analyzed by capillary electrophoresis using LIF detection according to the procedures described above. FIG. 4 illustrates the results of these tests. Electropherogram a) shows Cy5.5 labeled PCP and Cy5 labeled morphine at concentrations of 10 nM prior to titrating. Electropherogram b) shows the results of titrating with morphine antibody with results similar to that shown in EXAMPLE 2. Electropherogram c) shows the results of titrating with PCP antibody. Here it can be seen that the Cy5 labeled morphine-antibody complex and the Cy5.5 labeled PCP-antibody complex do not resolve by these CE methods. However as shown in electropherograms b), c), and d), the peaks associated with the labeled drugs are resolved and their signal will change with the concentration of any competing species in the immunoassay system.

EXAMPLE 6

Figure 5:
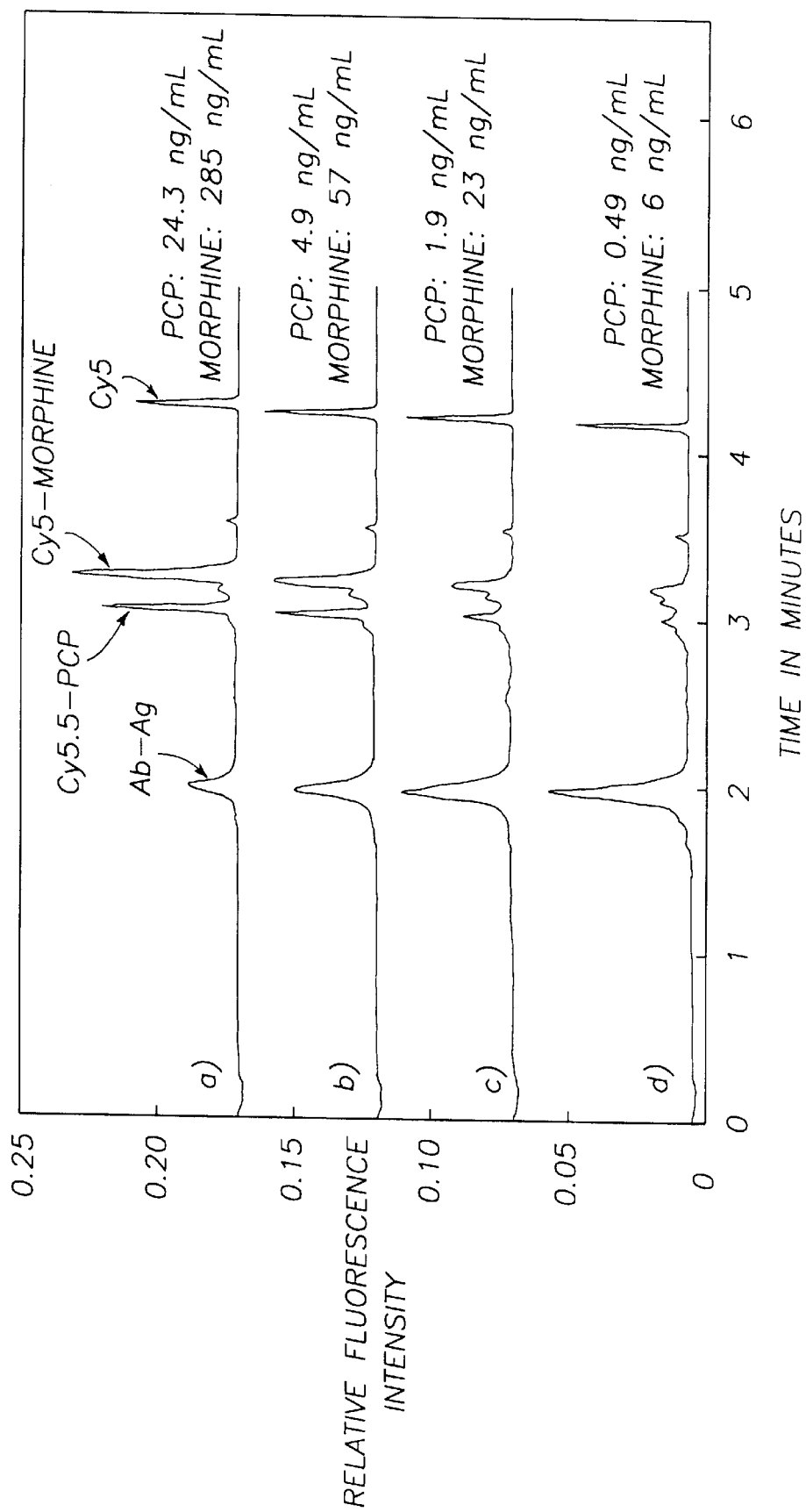
FIG. 5 shows electropherograms of the simultaneous assay of morphine and PCP by CE LIF. Electropherograms a), b), c), and d) show the results of different simultaneous immunoassays using different concentrations of drug.

The ability to simultaneously assay morphine and PCP, even though their antibody complexes are not resolved using CE-LIF procedures, is shown in FIG. 5. Here, the labeled drugs were reacted in the presence of varying amount of PCP and morphine. As can be seen by electropherogram a), b), c), and d), these the peaks associated with the labeled drugs are resolved and their size is proportional to the amount of unlabeled analyte present in the immunoassay system.

The above examples demonstrate the simultaneous competitive immunoassay of morphine, PCP, theophylline, and digoxinenin in urine samples. The appearance of the fluoro (Cy5 or Cy5.5) labeled drug peak is proportional to the drug species present in the urine sample. Quantitation of the analytes can be achieved by using internal standard, Cy5 or Cy5.5 in the assay mixture. The simultaneous analysis of analytes in accordance with the present invention can be performed routinely and reproducibly in less than 5 minutes with an analytical sensitivity of $10^{-10}$.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

What is claimed is:

1. A method for simultaneously assaying a plurality of analytes in a sample, the method comprising the steps of:

(A) incubating the sample potentially containing a first analyte and a second analyte in the presence of i) a judicious amount of the first analyte labeled with a fluorophore and a judicious amount of the second analyte labeled with a fluorophore, ii) a first antibody capable of specifically binding to the first analyte to create first antibody-analyte complex and capable of specifically binding to the first analyte labeled with a fluorophore to create first antibody-labeled-analyte complex; and iii) a second antibody capable of specifically binding to the second analyte to create second antibody-analyte complex and capable of binding to the second analyte labeled with a fluorophore to create second antibody-labeled-analyte complex, wherein the incubation is conducted under conditions sufficient to permit creation of first antibody-analyte complex, first antibody-labeled-analyte complex, second antibody-analyte complex and second antibody-labeled-analyte complex;

(B) subjecting an amount of incubated sample of step (A) to capillary electrophoresis, the capillary electrophoresis being conducted under conditions to separate first antibody-analyte complex and first antibody-labeled-analyte complex from first labeled-analyte, and to separate second antibody-analyte complex and second antibody-labeled-analyte complex from second labeled-analyte;

wherein the conditions under which capillary electrophoresis are conducted are not sufficient to separate first antibody-analyte complex from the second antibody-analyte complex; and (C) detecting each of the fluorophore labels by inducing fluorescence of the fluorophores, and detecting the induced fluorescence.

2. The method of clam 1, wherein at least one of the plurality of analytes is selected from the group consisting of therapeutic drugs, drugs of abuse, environmental toxins and proteins.

3. The method of claim 1, wherein the sample is selected from the group consisting of blood, serum, urine, water, waste, foodstuff, and milk.

4. The method of clam 1, wherein at least one of the plurality of analytes is selected from the group consisting of morphine, digoxinenin, PCP and theophyllin.

5. The method of clam 1 wherein at least one of the plurality of analytes is present in the sample at a concentration less than about $10^{-10}$M.

6. The method of claim 1, wherein in step (A), the first antibody or the second antibody is selected from the group consisting of a polyclonal antibody, a monoclonal antibody, an Fab fragment and an $F(ab)_2$ fragment.

7. The method of claim 1, wherein in step (A), the fluorophore is selected from the group consisting of cyanines, fluorescein, isothiocyanate, rhodamine, phycoerythrin, phycocyanin, allophycocyanin, o-phthaldehyde label, fluorescamine, tetramethylrhodamine and BODIPY.

8. The method of claim 1, wherein in step (B), the capillary electrophoresis is conducted in an uncoated, fused silica column.

9. The method of claim 1, wherein in step (C), the induction of fluorescence is a laser-mediated induction of fluorescence.

10. The method of claim 1, wherein the analytes labeled with a fluorophore are formed by reacting the analytes or an analyte derivative with a fluorescing cyanine dye.

11. The method of claim 10, wherein the fluorescing cyanine dye has the formula:

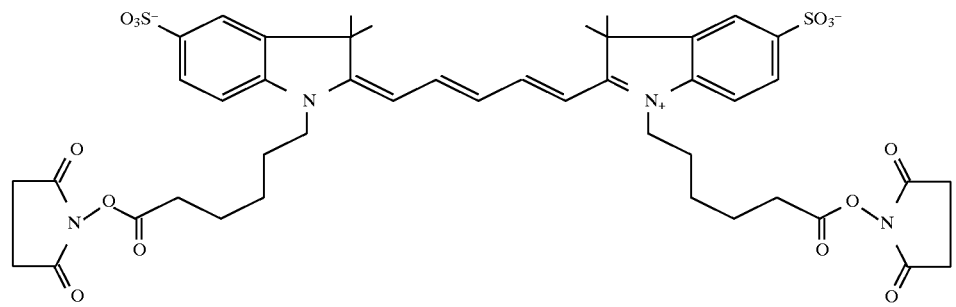

12. The method of claim 10, wherein the fluorescing cyanine dye has the formula:

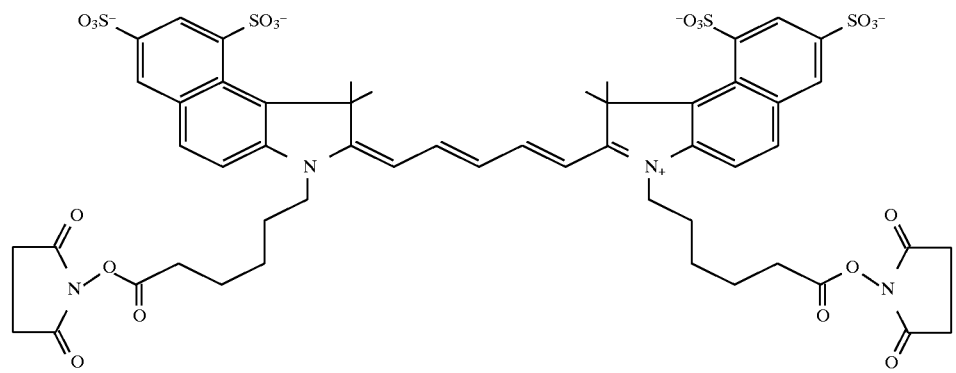

13. The method of claim 1, wherein the sample is a clinical urine sample.

* * * * *